United States Patent
Kimura et al.

(10) Patent No.: US 8,894,671 B2
(45) Date of Patent: Nov. 25, 2014

(54) HEMOSTATIC CLIP

(71) Applicant: Olympus Medical Systems Corp., Tokyo (JP)

(72) Inventors: Ko Kimura, Tokyo (JP); Kensuke Uesaka, Tokyo (JP); Hideki Fujii, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 14/273,993

(22) Filed: May 9, 2014

(65) Prior Publication Data

US 2014/0249553 A1 Sep. 4, 2014

Related U.S. Application Data

(63) Continuation of application No. PCT/JP2013/068089, filed on Jul. 2, 2013.

(60) Provisional application No. 61/673,964, filed on Jul. 20, 2012.

(51) Int. Cl.
*A61B 17/12* (2006.01)
*A61B 17/122* (2006.01)

(52) U.S. Cl.
CPC ..... *A61B 17/122* (2013.01); *A61B 2017/12004* (2013.01)
USPC ............................................ 606/157; 24/537

(58) Field of Classification Search
None
See application file for complete search history.

(56) References Cited

U.S. PATENT DOCUMENTS

| 5,520,701 | A | * | 5/1996 | Lerch | 606/142 |
| 5,713,911 | A | | 2/1998 | Racenet et al. | |
| 6,001,110 | A | * | 12/1999 | Adams | 606/151 |
| 6,193,732 | B1 | * | 2/2001 | Frantzen et al. | 606/151 |
| 6,638,297 | B1 | * | 10/2003 | Huitema | 606/219 |

FOREIGN PATENT DOCUMENTS

| JP | A-2004-351211 | 12/2004 |
| JP | A-2005-58627 | 3/2005 |
| JP | A-2006-55287 | 3/2006 |
| JP | A-2007-196012 | 8/2007 |
| JP | B2-4870139 | 2/2012 |

OTHER PUBLICATIONS

International Search Report issued in International Patent Application No. PCT/JP2013/068089 dated Aug. 6, 2013 (with translation).

* cited by examiner

*Primary Examiner* — Tuan V Nguyen
(74) *Attorney, Agent, or Firm* — Oliff PLC

(57) ABSTRACT

A hemostatic clip includes: a clip body formed by folding an intermediate section of a belt-like member; and a holding tube. The clip body includes: a first member formed of a first metallic material that is elastically deformable; and a pair of second members that are formed of a second metallic material having a lower elastic strain limit than an elastic strain limit of the first metallic member and are connected to respective both ends of the first member. The holding tube is configured to change an opening width of the clip body by holding part of the clip body in the holding tube.

9 Claims, 4 Drawing Sheets

HEMOSTATIC CLIP

This application is a continuation application based on a PCT Patent Application No. PCT/JP2013/068089, filed Jul. 2, 2013, whose priority is claimed on U.S. Provisional Application No. 61/673,964, filed Jul. 20, 2012. The contents of both the PCT Application and the United States Provisional Application are incorporated herein by reference.

BACKGROUND OF THE INVENTION

1. Field of the Invention

The present invention relates to a hemostatic clip that is introduced into a body cavity through an endoscope and used in the body cavity. Particularly, the present invention relates to the hemostatic clip capable of re-ligating target tissue.

2. Description of Related Art

Conventionally, bleeding of a digestive canal is stopped by introducing a hemostatic clip into a body cavity through an endoscope and pinching (ligating) a bleeding spot using the hemostatic clip (e.g., see Japanese Unexamined Patent Application, First Publication No. 2007-196012).

When such a hemostatic clip is used, the bleeding may not be successfully stopped by ligating the bleeding spot once. In such cases, it is convenient that the clip can be reopened and the bleeding spot can be pinched again more properly using the clip. However, it is not easy to reopen the clip because friction between part of the clip retracted into a fixing member such as a holding tube during the pinching produces and the fixing member is generated.

A hemostatic clip capable of re-ligating is disclosed in Japanese Patent No. 4870139. In this hemostatic clip, an elastic part biasing the clip against a fixing member in an advancing direction is provided in the fixing member. As a result, the clip is relatively easily pushed out even after the clip is retracted into the fixing member once, and thus it is not so difficult to reopen the clip.

SUMMARY OF THE INVENTION

According to a first aspect of the present invention, a hemostatic clip includes: a clip body formed by folding an intermediate section of a belt-like member; and a holding tube. The clip body includes: a first member formed of a first metallic material that is elastically deformable; and a pair of second members that are formed of a second metallic material having a lower elastic strain limit than an elastic strain limit of the first metallic material and are connected to respective both ends of the first member. The holding tube is configured to change an opening width of the clip body by holding part of the clip body in the holding tube.

According to a second aspect of the present invention, in the hemostatic clip according to the first aspect of the present invention, the first member may include: a bending point formed by folding part of the first member that is in a middle of the both ends of the first member; and enlarged sections that are formed in the respective both ends of the first member and extend to be bent in a direction in which the enlarged sections separate from each other. The second members connected to the respective enlarged sections may be configured to come close to each other as part of the enlarged sections are held in the holding tube.

According to a third aspect of the present invention, in the hemostatic clip according to the second aspect of the present invention, the enlarged sections may have respective elastic deformation sections configured to be elastically deformed in a direction in which the elastic deformation sections come close to each other by a distal end section of the holding tube pushing the elastic deformation sections.

According to a fourth aspect of the present invention, in the hemostatic clip according to the third aspect of the present invention, the first member may be configured to be elastically deformed when the second members are at a position where distal end sections of the second members come close to each other.

According to a fifth aspect of the present invention, in the hemostatic clip according to the fourth aspect of the present invention, one of the both ends of the first member and an end of one of the second members may be stacked and joined.

According to a sixth aspect of the present invention, in the hemostatic clip according to the fifth aspect of the present invention, the first member and the second members may be joined by metallic bonding.

According to a seventh aspect of the present invention, in the hemostatic clip according to the sixth aspect of the present invention, the clip body may be formed by a process of removing part of a multi-layered metal sheet in which the first member and the second members are stacked and joined by the metallic bonding.

According to an eighth aspect of the present invention, in the hemostatic clip according to the sixth aspect of the present invention, the first member and the second members may constitute a cladding material in which the first member and the second members are stacked through the metallic bonding.

According to a ninth aspect of the present invention, in the hemostatic clip according to the fifth aspect of the present invention, the first member and the second members may be joined by welding.

DETAILED DESCRIPTION OF THE INVENTION

A hemostatic clip according to an embodiment of the present invention is described with reference to FIGS. 1 to 7.

Figure 1:
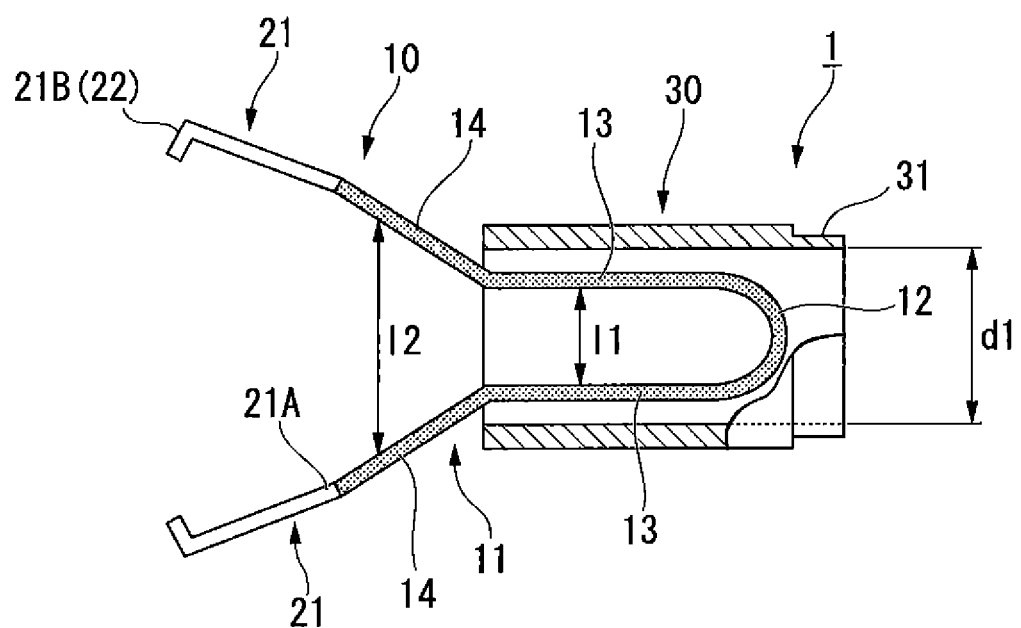
FIG. 1 is a partial cross-sectional view showing the constitution of a hemostatic clip according to an embodiment of the present invention.

As shown in FIG. 1, a hemostatic clip 1 according to the present embodiment includes a clip body 10 and a holding tube 30. The clip body 10 is formed by folding an intermediate section of a belt-like member, and pinches and ligates tissue. As part of the clip body 10 is held in the holding tube 30, the holding tube 30 changes an opening width of the clip body 10.

The clip body 10 includes a first member 11 and a pair of second members 21. The first member 11 is formed in such a manner that a belt-like metal is folded at a longitudinal middle section thereof. The second members 21 are connected to respective both longitudinal ends of the first member 11.

The first member 11 includes two parallel sections 13 and two enlarged sections (elastic deformation sections) 14. The two parallel sections 13 extend from a bending point 12 in parallel (or approximately parallel) with each other. The enlarged sections 14 are each formed by bending part of each parallel section 13, and extend away from each other.

Figure 7:
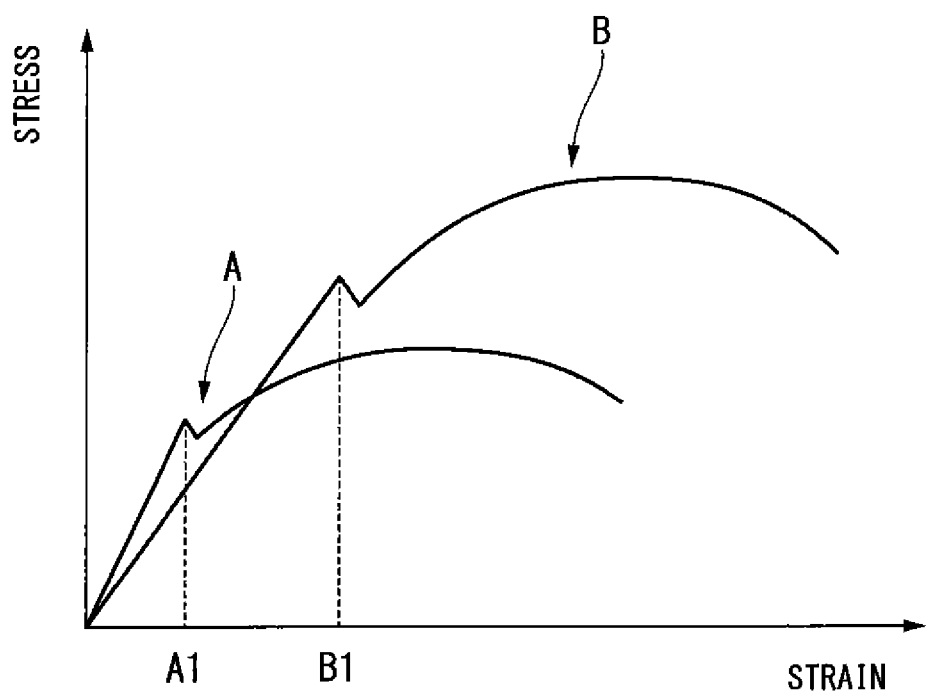
FIG. 7 is a view showing an example of a stress-strain curve of a material used for the hemostatic clip according to the embodiment of the present invention.

The first member 11 is formed of an elastically deformable metallic material (a first metallic material). As the first metallic material, a metallic material having higher yield strength than that of stainless steel (e.g., SUS304 defined by JIS) that is a typical material for the hemostatic clip is preferably used. Such a metallic material has a wider elastic deformation range than that of the stainless steel, i.e., a higher elastic strain limit than that of the stainless steel. The elastic strain limit is a value given by dividing yield strength of a material by a Young's modulus of the material. As shown in FIG. 7, when a stress-strain curve of the stainless steel is, for instance, a stress-strain curve A, a stress-strain curve of the first member 11 may be a stress-strain curve B having an elastic strain limit B1 higher than an elastic strain limit A1. In detail, for example, an amorphous alloy called metallic glass, β titanium or an alloy thereof may be used as the first metallic material.

The second members 21 are formed of a belt-like metal having an approximately linear shape. A first end 21A of each of the second members 21 is connected to the first member 11. The second members 21 extend away from each other in order to be connected to the enlarged sections 14. A second end 21B of each of the second members 21 is bent to an inner side in an opening and closing direction of the clip body 10 and makes up a claw 22.

The second members 21 are formed of a metallic material (a second metallic material) having a lower elastic strain limit than that of the first metallic material. The Young's modulus of the second metallic material may be greater than that of the first metallic material. In this case, rigidity of the second members 21 is greater than that of the first metallic material. To be specific, stainless steel or a cobalt-chromium (Co—Cr) alloy may be used as a material for the second members 21.

Figure 2:
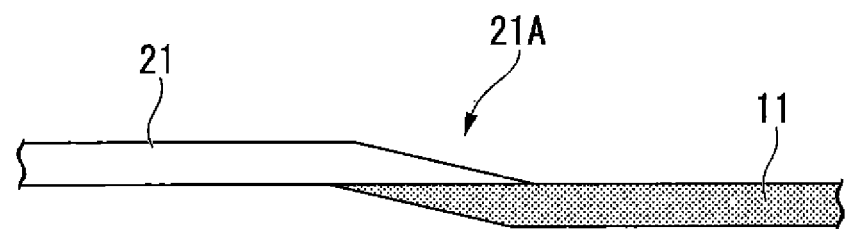
FIG. 2 is an enlarged view of a connecting portion between a first member and a second member in the hemostatic clip according to the embodiment of the present invention.

FIG. 2 is an enlarged view of a connecting portion between the first member 11 and the second member 21. An end of the first member 11 and an end of the second member 21 are firmly joined by metallic bonding while overlapping in a thickness direction. The stacking order in which they are joined is not particularly limited.

Figure 3A:
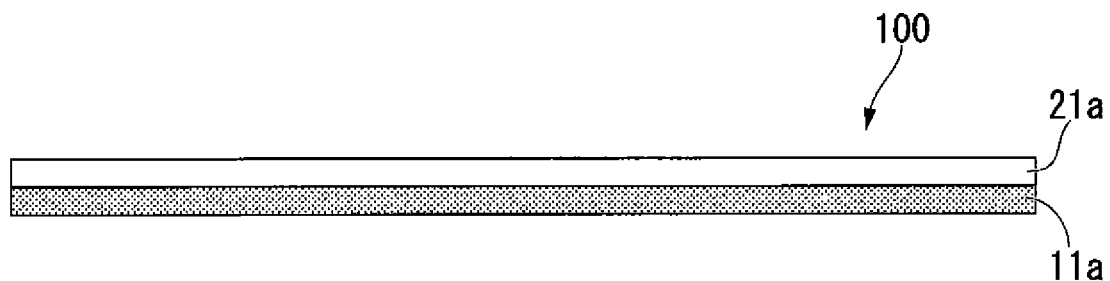
FIG. 3A is a view showing an example of a manufacturing procedure of a clip body in the hemostatic clip according to the embodiment of the present invention.
Figure 3B:
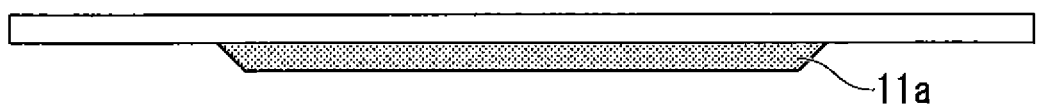
FIG. 3B is a view showing the example of the manufacturing procedure of the clip body in the hemostatic clip according to the embodiment of the present invention.
Figure 3C:
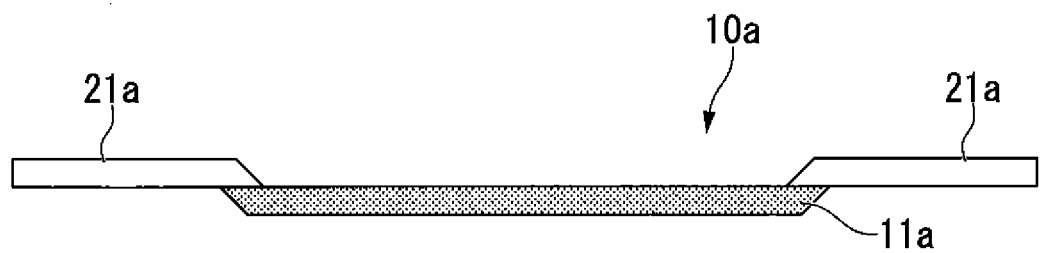
FIG. 3C is a view showing the example of the manufacturing procedure of the clip body in the hemostatic clip according to the embodiment of the present invention.

The first member 11 and the second member 21 that are joined as described above may be appropriately manufactured using, for instance, a cladding material 100 as shown in FIG. 3A. In detail, first, the cladding material 100 having a two-layer structure in which a material 11a of the first member 11 and a material 21a of the second member 21 are stacked is prepared. Next, as shown in FIG. 3B, the material 11a corresponding to a region having a length required as the second member 21 is removed from both ends of the cladding material 100 by grinding or the like. On the region of the remaining middle section, as shown in FIG. 3C, the material 21a is removed by grinding or the like. As a result, a member 10a is manufactured in such a manner that the region of the middle section is made up of only the material 11a and that regions, which are made up of only the materials 21a and have a predetermined length, are formed at both ends of the region of the middle section. As the member 10a is folded at a longitudinal middle section thereof and predetermined portions thereof are bent or folded, the clip body 10 is completed.

In the cladding material of a multi-layered metal sheet, the metallic materials forming respective stacked layers are firmly joined by the metallic bonding. For this reason, the first member 11 and the second members 21 are almost never detached.

In the example of the foregoing manufacturing procedure, end faces of the materials 11a and 21a which are located at the connecting side are formed in a slope shape. However, this is not essential. When done in this way, the stress applied to the connecting portion is properly distributed, and the stress is not easily concentrated on a specific spot. Further, it may be properly determined which of the material 11a and the material 21a is ground first.

The holding tube 30 is formed of a metal such as stainless steel in a tubular shape. As shown in FIG. 1, one end of the holding tube 30 is provided with a tubular fitting section 31 having a smaller outer diameter than that of the other portion. The fitting section 31 is used when the hemostatic clip 1 is mounted on an indwelling device 110 to be described below.

An inner diameter d1 of the holding tube 30 is larger than a distance l1 between the two parallel sections 13. For this reason, the parallel sections 13 can advance and retract in the holding tube 30 without resistance. At least part of distances between the enlarged sections 14, i.e., a distance l2, is larger than the inner diameter d1.

With regard to movement of the hemostatic clip 1 according to the present embodiment configured as described above when the hemostatic clip 1 is used, a case in which hemostatic treatment of digestive canal bleeding is performed is described as an example.

After a surgical operator checks a bleeding position using an endoscope, the surgical operator engages an advancing and retracting member 111, which advances and retracts the clip body 10, with the bending point 12. In this state, the surgical operator inserts the fitting section 31 of the holding tube 30 into a distal end of an inserting part of the indwelling device 110 formed by a coil sheath or the like. The surgical operator mounts the hemostatic clip 1 on the indwelling device 110.

As the indwelling device 110, a widely known instrument equipped with a manipulation part for manipulating a hemostatic clip at a proximal end of the long inserting part may be used. In the event of shipment, the hemostatic clip 1 may be previously mounted on the indwelling device 110.

The surgical operator inserts a distal end side of the indwelling device 110 on which the hemostatic clip 1 is mounted from a forceps opening of the endoscope into a surgical device channel of the endoscope. The surgical operator introduces the hemostatic clip 1 up to a bleeding site via the endoscope. The surgical operator causes the hemostatic clip 1 to protrude from a surgical device channel opening of a distal end section of the endoscope.

Figure 4:
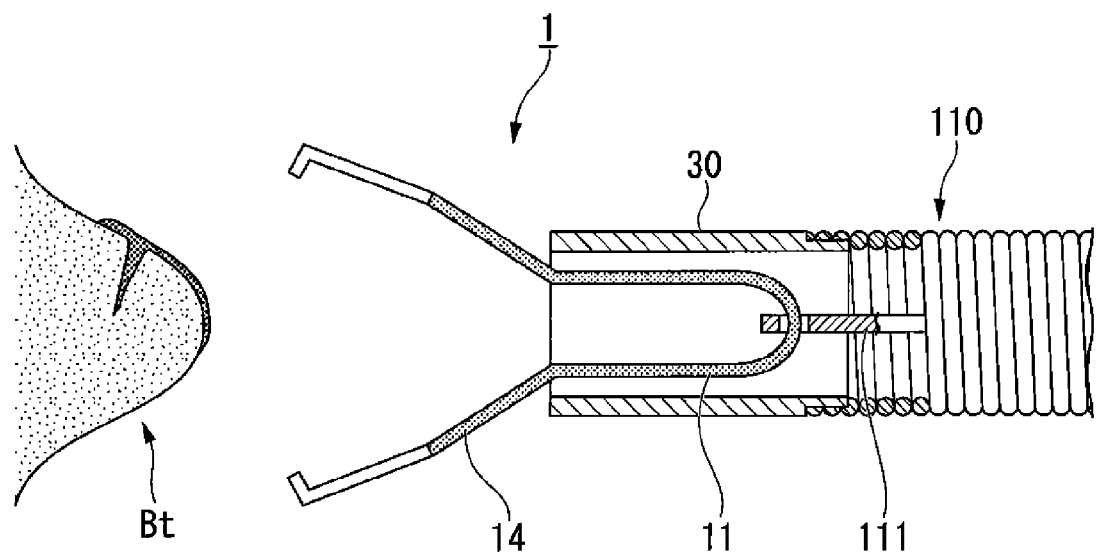
FIG. 4 is a view showing movement of the hemostatic clip according to the embodiment of the present invention when the hemostatic clip is used.

As shown in FIG. 4, the surgical operator brings the hemostatic clip 1 in close proximity to a bleeding site Bt while checking an endoscopic image. After the surgical operator positions the pair of second members 21 so as to pinch the bleeding site Bt, the surgical operator manipulates the manipulation part (not shown) of the indwelling device 110, and retracts the advancing and retracting member 111.

Figure 5:
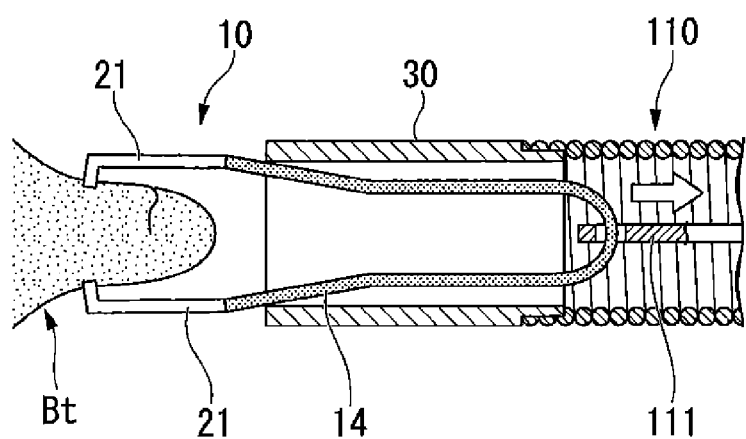
FIG. 5 is a view showing movement of the hemostatic clip according to the embodiment of the present invention when the hemostatic clip is used.

Thereby, the first member 11 engaged with the advancing and retracting member 111 is retracted relative to the holding tube 30. When the enlarged sections 14 of the first member 11 advance into the holding tube 30, the enlarged sections 14 are regulated in shape by the holding tube 30, and are elastically deformed to come close to each other in the holding tube 30. As a result, the second members 21 connected to the enlarged sections 14 also come close to each other. As shown in FIG. 5, the clip body 10 pinches the bleeding site Bt. At this point of time, since there is also a possibility of re-pinching, the surgical operator holds the manipulation part in a state of "provisional ligation" without advancing the second members 21 into the holding tube 30.

In the state of the provisional ligation, the surgical operator checks an endoscope screen, and checks whether bleeding is actually stopped. When bleeding is discovered despite the provisional ligation of the bleeding site Bt, the pinching of the hemostatic clip 1 may be improper. Thus, the surgical operator manipulates the manipulation part to advance the advancing and retracting member 111. This manipulation causes the clip body 10 to be opened to release the ligation of the bleeding site Bt.

The surgical operator manipulates the endoscope and the indwelling device 110 to adjust a position and a direction of the hemostatic clip 1 to the bleeding site Bt. The surgical operator provisionally ligates the bleeding site Bt again, and checks whether the bleeding is stopped. The surgical operator repeats similar manipulation multiple times as needed until the bleeding is reliably stopped.

Since the first member 11 is formed of the metallic material having the wider elastic deformation range than that of the stainless steel, even when the enlarged sections 14 repeat entrance into and exit from the holding tube 30 multiple times, the enlarged sections 14 are not easily deformed plastically. Accordingly, the opening width of the enlarged sections 14 is inhibited from being narrowed with the repetition of the provisional ligation. When the enlarged sections 14 come out of the holding tube 30, an initial opening width of the enlarged sections 14 as shown in FIG. 4 is kept well.

Figure 6:
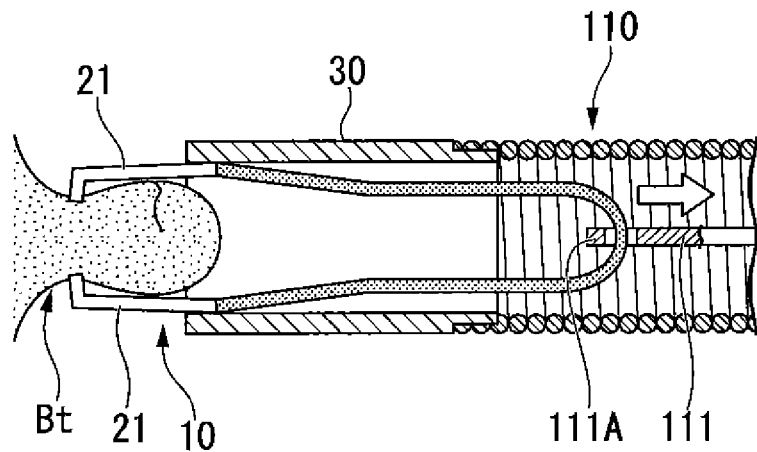
FIG. 6 is a view showing movement of the hemostatic clip according to the embodiment of the present invention when the hemostatic clip is used.

In the state of the provisional ligation, when it has been determined that the bleeding is stopped, the surgical operator manipulates the manipulation part to further retract the advancing and retracting member 111. Thereby, as shown in FIG. 6, the second members 21 enter the holding tube 30. When the advancing and retracting member 111 is further retracted, a distal end section 111A of the advancing and retracting member 111 is deformed, and the engagement of the advancing and retracting member 111 with the clip body 10 is released. When the indwelling device 110 is retracted, the holding tube 30 is detached from the indwelling device 110, and placing of the hemostatic clip 1 is completed.

In the state in which the hemostatic clip 1 is placed, since the second members 21 are in contact with the holding tube 30, a force ligating the bleeding site Bt is defined by the second members 21 having the rigidity equal to or greater than that of the first metallic material. For this reason, the hemostatic clip 1 reliably ligates the bleeding site Bt, and the hemostatic state is favorably maintained.

When the hemostatic clip set forth in Japanese Patent No. 4870139 above is retracted into the fixing member, part of the clip is plastically deformed in a closing direction. For this reason, even when the clip is pushed out of the fixing member, an opening width of the clip becomes slightly narrow rather than returning to its size prior to being retracted. When this movement is repeated, the opening width of the clip is further narrowed. As a result, there is a problem in that, although the clip can perform re-pinching, the ligation of the bleeding spot is difficult because the opening width of the clip is narrow.

In the hemostatic clip 1 according to the present embodiment, the first member 11 formed of the metallic material having the wider elastic deformation range than that of the stainless steel is provided. For this reason, as the provisional ligation is performed by advancing the first member 11 into the holding tube 30, even when the provisional ligation is repeated, the first member 11 nearly returns to an initial state, and the opening width of the hemostatic clip 1 is hardly reduced. As a result, it is possible to provide the hemostatic clip 1 as a handy hemostatic clip which easily performs re-pinching.

The second members 21 having the rigidity equal to or greater than that of the first metallic material are connected to the first member 11. For this reason, after the provisional ligation is performed under proper conditions, the second members 21 are partly held in the holding tube 30, and thereby the target tissue such as the bleeding site Bt can be reliably ligated with a strong force.

In this way, in the hemostatic clip 1 according to the present embodiment, both easy re-pinching and a high ligating force that are hard to obtain with a single material are compatible.

The first member 11 and the second members 21 are firmly connected by the metallic bonding. For this reason, although two types of materials are used, the surgical operator can use the hemostatic clip 1 with no particular concern for things such as detachment of the materials.

In the aforementioned hemostatic clip, the clip body may be manufactured without using the aforementioned cladding material. For example, the first member and the second members may be joined by welding. In this case, since they are not connected by the metallic bonding, joining strength is slightly weakened, but an effect can be obtained to some extent.

In the aforementioned hemostatic clip, the parallel sections are not essential. Thus, the first member may be formed such that part of the first member closer to the bending point than the enlarged sections is not parallel and is mutually separated at a narrower opening width than that of the enlarged sections. The first member may be configured such that the enlarged sections are formed in part of the first member adjacent to the vicinity of the bending point.

In the aforementioned hemostatic clip, the clip body may include a first member formed of a metallic material having a wider elastic deformation range than that of stainless steel, and a pair of second members formed of a metallic material having a Young's modulus equal to or greater than that of the stainless steel and connected to respective both ends of the first member.

Hereinabove, while a preferred embodiment of the present invention have been described, the present invention is not limited to the embodiment. Additions, omissions, substitutions, and other modifications can be made to the present invention without departing from the spirit and scope of the present invention. The present invention is not limited by the above-mentioned description, and is only limited by the scope of the appended claims.

What is claimed is:

1. A hemostatic clip comprising:
    a clip body formed by folding an intermediate section of a belt-like member, and
    a holding tube, wherein
    the clip body includes:
        a first member formed of a first metallic material that is elastically deformable; and
        a pair of second members that are formed of a second metallic material having a lower elastic strain limit than an elastic strain limit of the first metallic material and are connected to respective both ends of the first member, and the holding tube is configured to change an opening width of the clip body by holding part of the clip body in the holding tube.

2. The hemostatic clip according to claim 1, wherein the first member includes:

a bending point formed by folding part of the first member that is in a middle of the both ends of the first member; and enlarged sections that are formed in the respective both ends of the first member and extend to be bent in a direction in which the enlarged sections separate from each other, and the second members connected to the respective enlarged sections are configured to come close to each other as part of the enlarged sections are held in the holding tube.

3. The hemostatic clip according to claim 2, wherein the enlarged sections have respective elastic deformation sections configured to be elastically deformed in a direction in which the elastic deformation sections come close to each other by a distal end section of the holding tube pushing the elastic deformation sections.

4. The hemostatic clip according to claim 3, wherein the first member is configured to be elastically deformed when the second members are at a position where distal end sections of the second members come close to each other.

5. The hemostatic clip according to claim 4, wherein one of the both ends of the first member and an end of one of the second members are stacked and joined.

6. The hemostatic clip according to claim 5, wherein the first member and the second members are joined by metallic bonding.

7. The hemostatic clip according to claim 6, wherein the clip body is formed by a process of removing part of a multi-layered metal sheet in which the first member and the second members are stacked and joined by the metallic bonding.

8. The hemostatic clip according to claim 6, wherein the first member and the second members constitute a cladding material in which the first member and the second members are stacked through the metallic bonding.

9. The hemostatic clip according to claim 5, wherein the first member and the second members are joined by welding.

* * * * *